(12) United States Patent
Mohammadi

(10) Patent No.: US 11,490,865 B2
(45) Date of Patent: Nov. 8, 2022

(54) C-ARM X-RAY APPARATUS

(71) Applicant: ESSPEN GmbH, Erlangen (DE)

(72) Inventor: Zahra Mohammadi, Erlangen (DE)

(73) Assignee: ESSPEN GmbH, Erlangen (DE)

( * ) Notice: Subject to any disclaimer, the term of this patent is extended or adjusted under 35 U.S.C. 154(b) by 0 days.

(21) Appl. No.: 16/649,603

(22) PCT Filed: Sep. 21, 2018

(86) PCT No.: PCT/EP2018/025240
§ 371 (c)(1),
(2) Date: Mar. 20, 2020

(87) PCT Pub. No.: WO2019/057339
PCT Pub. Date: Mar. 28, 2019

(65) Prior Publication Data
US 2020/0284737 A1    Sep. 10, 2020

(30) Foreign Application Priority Data
Sep. 21, 2017   (DE) ......................... 102017008921.3

(51) Int. Cl.
*A61B 6/02*    (2006.01)
*A61B 6/00*    (2006.01)
(Continued)

(52) U.S. Cl.
CPC ............ *A61B 6/4028* (2013.01); *A61B 6/025* (2013.01); *A61B 6/4007* (2013.01); *A61B 6/4441* (2013.01); *H01J 35/065* (2013.01); *H01J 35/24* (2013.01); *H01J 35/26* (2013.01); *H05G 1/70* (2013.01); *A61B 6/035* (2013.01);
(Continued)

(58) Field of Classification Search
None
See application file for complete search history.

(56) References Cited

U.S. PATENT DOCUMENTS 5,224,147 A * 6/1993 Collin .................. G03B 42/047
378/162
5,590,166 A * 12/1996 Suni ..................... A61B 6/0414
378/196
(Continued)

FOREIGN PATENT DOCUMENTS

DE    102008059455 A1    6/2010
DE    102009033607 A1    1/2011
(Continued)

OTHER PUBLICATIONS

Qian et al., "Design and characterization of a spatialy distributed multibeam filed emission x-ray source for stationary digital breast tomosynthesis", Medical Physics, vol. 36, No. 10:4389-4399 (2009).
(Continued)

*Primary Examiner* — Thomas R Artman
(74) *Attorney, Agent, or Firm* — Merchant & Gould P.C.

(57) ABSTRACT

A C-arm X-ray apparatus includes an x-ray emitter (5) and an X-ray detector (4) which are maintained on a C-arm (2) mounted on a reference plane. The x-ray emitter (5) has nanorods as electron emitters and has an elongated structure which is at least partially aligned along a surface normal of the reference plane.

23 Claims, 18 Drawing Sheets

(51) Int. Cl.
  *H01J 35/06* (2006.01)
  *H01J 35/24* (2006.01)
  *H01J 35/26* (2006.01)
  *H05G 1/70* (2006.01)
  *A61B 6/03* (2006.01)
  *H05G 1/58* (2006.01)

(52) U.S. Cl.
  CPC ..... *A61B 6/4405* (2013.01); *A61B 2560/0437* (2013.01); *H01J 2201/30469* (2013.01); *H05G 1/58* (2013.01)

(56) References Cited

U.S. PATENT DOCUMENTS

| | | | | |
|---|---|---|---|---|
| 7,085,346 | B1* | 8/2006 | Virta | A61B 6/4283 |
| | | | | 378/37 |
| 7,180,978 | B2* | 2/2007 | McKenna | A61B 6/0414 |
| | | | | 378/37 |
| 7,627,087 | B2* | 12/2009 | Zou | H01J 1/304 |
| | | | | 378/122 |
| 8,229,074 | B2* | 7/2012 | Mahapatra | H01J 35/065 |
| | | | | 378/122 |
| 8,559,591 | B2 | 10/2013 | Boese et al. | |
| 8,817,947 | B2* | 8/2014 | Vedantham | A61B 6/022 |
| | | | | 378/21 |
| 9,510,798 | B2* | 12/2016 | Mao | A61B 6/502 |
| 10,002,445 | B2* | 6/2018 | Mistretta | A61B 6/4028 |
| 10,413,268 | B2* | 9/2019 | Wang | A61B 6/54 |
| 10,660,580 | B2* | 5/2020 | Heath | A61B 6/4007 |
| 2005/0100129 | A1* | 5/2005 | McKenna | A61B 6/0414 |
| | | | | 378/37 |
| 2007/0009081 | A1* | 1/2007 | Zhou | G01N 23/046 |
| | | | | 378/10 |
| 2009/0003529 | A1* | 1/2009 | Zou | H01J 1/304 |
| | | | | 378/122 |
| 2011/0038465 | A1* | 2/2011 | Mahapatra | H01J 35/065 |
| | | | | 378/143 |
| 2011/0075809 | A1* | 3/2011 | Boese | A61B 6/4014 |
| | | | | 378/92 |
| 2012/0008739 | A1* | 1/2012 | Hoernig | A61B 6/502 |
| | | | | 378/37 |
| 2012/0027173 | A1* | 2/2012 | Duerr | G01N 23/04 |
| | | | | 378/62 |
| 2012/0195403 | A1* | 8/2012 | Vedantham | A61B 6/5282 |
| | | | | 378/4 |
| 2015/0043712 | A1* | 2/2015 | Wang | A61B 6/4028 |
| | | | | 378/42 |
| 2016/0089093 | A1* | 3/2016 | Mao | A61B 6/4441 |
| | | | | 378/198 |
| 2016/0256128 | A1* | 9/2016 | Wang | H01J 35/06 |
| 2017/0249758 | A1* | 8/2017 | Mistretta | G06T 11/006 |
| 2019/0350552 | A1* | 11/2019 | Wang | A61B 6/4405 |
| 2020/0284737 | A1* | 9/2020 | Mohammadi | A61B 6/4007 |

FOREIGN PATENT DOCUMENTS

| | | |
|---|---|---|
| DE | 102009043421 A1 | 4/2011 |
| DE | 102009058266 A1 | 9/2011 |
| DE | 102010018715 A1 | 11/2011 |
| DE | 102010028438 A1 | 11/2011 |
| DE | 102011006505 A1 | 10/2012 |
| WO | 2018/086737 A1 | 5/2018 |
| WO | 2018/141485 A1 | 8/2018 |

OTHER PUBLICATIONS

International Search Report and Written Opinion for PCT/EP2018/025240, dated Feb. 26, 2019.

Search Report for German Patent Application No. 102017008921.3, dated Jun. 5, 2018.

* cited by examiner

C-ARM X-RAY APPARATUS

This application is a National Stage Application of PCT/EP2018/025240, filed Sep. 21, 2018, which claims the benefit of German Patent Application No. 102017008921.3, filed Sep. 21, 2017, and which applications are incorporated herein by reference. To the extent appropriate, a claim of priority is made to each of the above-disclosed applications.

The invention relates to a C-arm X-ray apparatus, that is, an X-ray apparatus which has a C-shaped arm on which X-ray emitters and an associated X-ray detector are held. The invention further relates to a method for operating such a C-arm X-ray apparatus.

Various C-arm X-ray apparatuses are known, for example from documents DE 10 2009 033 607 A1, DE 10 2008 059 455 A1, and U.S. Pat. No. 8,559,591 B2. In the latter case, an X-ray source includes field emission cathodes based on carbon nanotubes (carbon nanotube (CNT) cathode).

A mobile C-arm X-ray apparatus is disclosed, for example, in DE 10 2011 006 505 A1.

C-arm X-ray apparatuses comprise emitter-detector arrangements, which are fastened to a substantially C-shaped carrier, that is, a C-arm. C-arm X-ray apparatuses are used in clinics, for example, for intraoperative imaging.

The underlying problem of the invention is to provide a C-arm X-ray apparatus with extended imaging options compared to prior art.

This problem is solved, according to the invention, by a C-arm X-ray apparatus having the features of claim 1. The C-arm of the X-ray apparatus defines a plane which is defined as reference plane. The "C" formed by the arm is thus located in the reference plane. The C-arm holds at least one X-ray emitter and an associated X-ray detector, wherein at least one of the X-ray emitters includes nanorods, particularly carbon nanotubes (CNT) for field emission of electrons. This X-ray emitter is at least partially aligned along a surface normal of the reference plane. This means that the X-ray emitter defines an elongate, for example tube-like structure, which has at least one section extending orthogonally to the reference plane. The C-arm X-ray apparatus thus differs in principle from prior art C-arm devices as disclosed, for example, in document U.S. Pat. No. 8,559,591 B2 mentioned above, in which an arrangement of multiple X-ray sources is located in the reference plane. The transverse orientation of the X-ray emitter to the reference plane largely allows the generation of sectional images of an object under examination without any adjustment of the C-arm. This facilitates both time saving operation of the C-arm X-ray apparatus suitable for tomography and a high quality of generated image data.

In a simple design, the X-ray emitter of the C-arm X-ray apparatus according to the invention has a straight, elongate, substantially cylindrical shape. The center axis of the X-ray emitter, particularly the longitudinal axis of the cylinder, is identical herein to a surface normal of the reference plane.

In a modified design, the X-ray emitter has a curved shape, wherein a tangent placed at the center of the X-ray emitter represents a surface normal of the reference plane. Overall, the curved X-ray emitter defines a plane which is orthogonal relative to the reference plane. The curvature of the X-ray emitter can for example be designed in the shape of a circular arc or in a U-shape.

If one imagines the two ends of a U-shaped X-ray emitter joined together, the result would be an annular shape of the X-ray emitter. In such an embodiment, two tangents parallel to each other placed on the X-ray emitter each represent a surface normal of the reference plane defined by the C-arm. The annular X-ray emitter can either be designed as an open or as a closed ring. In the case of a closed ring, particularly a circular shape, the length of a closed line running centrally through the entire ring, particularly a circle, the diameter of which corresponds to the mean value between the inner diameter and the outer diameter of the overall annular X-ray emitter, indicates the entire extension of the X-ray emitter in the longitudinal direction of the elongate structure.

Instead of a ring shape, the emitter can also have a polygonal shape, for example. The extension of the X-ray emitter in the longitudinal direction is defined as the sum of the lengths of each side of the polygon, wherein the side lengths are to be measured in the center of the cross section of the X-ray emitter. Spatially, the polygon-shaped X-ray tube is a modification of a torus. An annular shape, that is, a torus shape, or a polygonal shape can also be formed by an arrangement of multiple X-ray emitters, each containing nanorods.

Regardless of whether the X-ray emitter is fully straight elongate or curved elongate, in an open arc or in a closed ring, the entire extension of the X-ray emitter as measured in each section of the elongate structure in its longitudinal direction is at least the quadruple of the maximum diameter of the cross section of the X-ray emitter as measured across its elongate structure.

The cathodes of the X-ray emitter provided to emit electrons preferably include carbon nanotubes as nanorods. The very high electrical and thermal conductivity of carbon nanotubes facilitates high current carrying capacity without significant heat generation of the individual carbon nanotubes themselves. Carbon nanotubes have a low field emission threshold of less than 2 V/m for the field emission of electrons. The field strength threshold value of cathodes for the emission of electrons, which cathodes comprise carbon nanotubes, can be lowered even more in that the carbon nanotubes are arranged in the vertical preferential direction on the cathode surface. Since single-wall carbon nanotubes are semiconductors and multi-wall carbon nanotubes are metallic conductors, multi-wall carbon nanotubes are particularly suited as electron emitters on the cathodes of the X-ray emitter.

Apart from carbon nanotubes, other types of nanorods, generally referred to as nanosticks, are suitable for emitting electrons within the X-ray emitter. In a preferred embodiment, field emission cathodes as cathodes of the X-ray tube are formed of such nanosticks.

The nanosticks of the cathode are preferably made of a material which has the lowest possible electron work function for the field emission of electrons with respect to the quantum mechanical field emission effect. The nanosticks comprise in this context an intrinsically homogeneous or heterogeneous composition and may either be configured as hollow bodies, that is, tubes, or as solid bodies. The cathodes may comprise nanosticks of the same type or a mixture of different types of nanosticks, wherein the term "type of nanosticks" refers to their material composition and material modification.

Suitable materials in pure or doted form for the field emission of electrons include, in addition to single or multi-wall carbon nanotubes, single or multi-wall heteronitrogen carbon nanotubes, borides of rare earth metals, particularly lanthanum hexaboride and cerium hexaboride, metal oxides, particularly $TiO_2$, MnO, ZnO, and $Al_2O_3$, metal sulfides, particularly molybdenum sulfide, nitrides, particularly boron nitride, aluminum nitride, carbon nitride, gallium nitride, carbides, particularly silicon carbide, silicon. Suitable parent products for producing the nanosticks, which emit electrons when the cathodes are in operation, include rod-shaped, optionally hollow, elements of polymeric materials. The nanosticks of the cathodes are optionally made of parent products which only partially include polymer materials, particularly in the form of a coating.

In a particularly preferred embodiment, the cathodes have nanosticks on their surfaces in a vertical preferential direction, that is, directed towards the anode of the X-ray emitter. When operating the X-ray emitter and at a sufficient distance from each other, very strong electrical fields can be generated at the tips of the nanosticks, whereby the emission of electrons is significantly simplified.

In a possible embodiment of the C-arm X-ray apparatus, more than one variety of cathodes is arranged in the vacuum tube of the X-ray emitter, wherein the term "variety" can refer both to the geometry and to other properties of the cathodes, for example materials. Cathodes of the same and different variety can in principle be sequentially electrically controlled in any manner. In addition to the cathodes, there may be differences with respect to focusing. This means that different electron beams and ultimately different X-ray beams can be generated in conjunction with properties such as the surface geometry of each cathode.

The nanorods of the cathode have for example a length of less than 20 μm and a diameter of less than 10 nm, wherein there is a density relative to the area of the cathode of at least $10^6$ nanorods per $cm^2$. A particularly suitable method for producing the nanorods is a screen printing method.

The X-ray emitters of the C-arm X-ray apparatus can be intended to generate various X-ray images, which differ with respect to dose, that is, to operate with a dose modulation. In general, X-rays of different wavelengths, as provided for multi-energy or dual-energy images, can be generated by different settings of the anode voltage. Multi-energy images particularly come into consideration in angiography.

As to the design of the X-ray emitter of the C-arm X-ray apparatus and the operation of the X-ray emitter, inter alia, any and all designs and methods can be implemented which are described in documents WO 2018/086737 A1 and WO 2018/141485 A1. The detector of the C-arm X-ray apparatus can for example be a line detector.

Regardless of the design of the at least one X-ray emitter, the C-arm X-ray apparatus can generate successive X-ray pulses of different wavelengths in a preferred process procedure. This makes it possible to distinguish different materials withing the volume to be examined with particularly high reliability and at the same time in a short recording time.

According to an advantageous further developed embodiment, the C-arm X-ray apparatus includes another X-ray emitter in addition to the at least one X-ray emitter which contains nanorods, particularly carbon nanotubes. In the case of an annular shape or polygonal shape of the CNT X-ray emitter or X-ray emitter including other nanorods, the additional X-ray emitter is preferably arranged centrally in the annular or polygonal X-ray emitter. In a preferred embodiment, the additional X-ray emitter allows emission of a higher X-ray dose compared to the previously mentioned emitter comprising nanorods. The additional X-ray emitter may particularly be an X-ray emitter having a rotating anode. A joint detector is associated with the X-ray emitter comprising nanorods for the emission of electrons and the other X-ray emitter. The additional X-ray emitter can in principle be an X-ray emitter of any design. Particularly, the additional X-ray emitter may comprise, like the annular or polygonal X-ray emitter, at least one cathode which contains nanorods, particularly carbon nanotubes. For example, the additional X-ray emitter contains three electron emitters, each of which are configured as surface emitters with nanorods. Particularly in a configuration of the additional X-ray emitter with nanorods, the anode of this X-ray emitter can be a non-rotating anode.

According to an alternative embodiment, the X-ray emitter and the X-ray detector can be pivoted jointly about an axis of rotation located in the reference plane. The rotational movements of the X-ray emitter and the X-ray detector are preferably electronically synchronized. This means that there is a joint virtual axis of rotation of the X-ray emitter and the X-ray detector. This embodiment is also suitable for a C-arm which cannot be pivoted as a whole and represents a mechanically simplified embodiment.

Where the X-ray emitter and the X-ray detector can be pivoted about the joint axis of rotation, the C-arm X-ray apparatus can be operated according to claim 17. In this process, multiple X-ray images are created which differ from each other, both with respect to the setting of the C-arm in its tangential direction and with respect to the angular setting of the X-ray emitter and the X-ray detector relative to their joint axis of rotation. Preferably, when creating a set of X-ray images, the C-arm is fixed in a first number of various positions with respect to its adjustment in the tangential direction, wherein X-ray images with a second number of various angular settings of X-ray emitter and X-ray detector, i.e. settings about said axis of rotation, are generated in each of these positions.

Pivotability of X-ray emitter and X-ray detector about said axis of rotation can for example be used for tomosynthesis and generally allows the creation of multi-plane images. Otherwise, the C-arm X-ray apparatus provides the option to create particularly high-quality X-ray images compared to conventional X-ray apparatuses with few or no extra devices, even if the X-ray emitter is not adjustable on the C-arm, due to the described design of the latter.

Multiple embodiments of the invention are explained in greater detail below with reference to a drawing. Wherein:

FIGS. 1 and 2 show a first embodiment of a C-arm X-ray apparatus in various operating positions, FIGS. 3 and 4 show a second embodiment of a C-arm X-ray apparatus, FIG. 5 shows a third embodiment of a C-arm X-ray apparatus, FIG. 6 shows a fourth embodiment of a C-arm X-ray apparatus, FIG. 7 shows a simplified view of a detail of the C-arm X-ray apparatus according to FIG. 1, illustrating the optical path of the X-ray radiation emitted from various X-ray sources.

Figure 5:
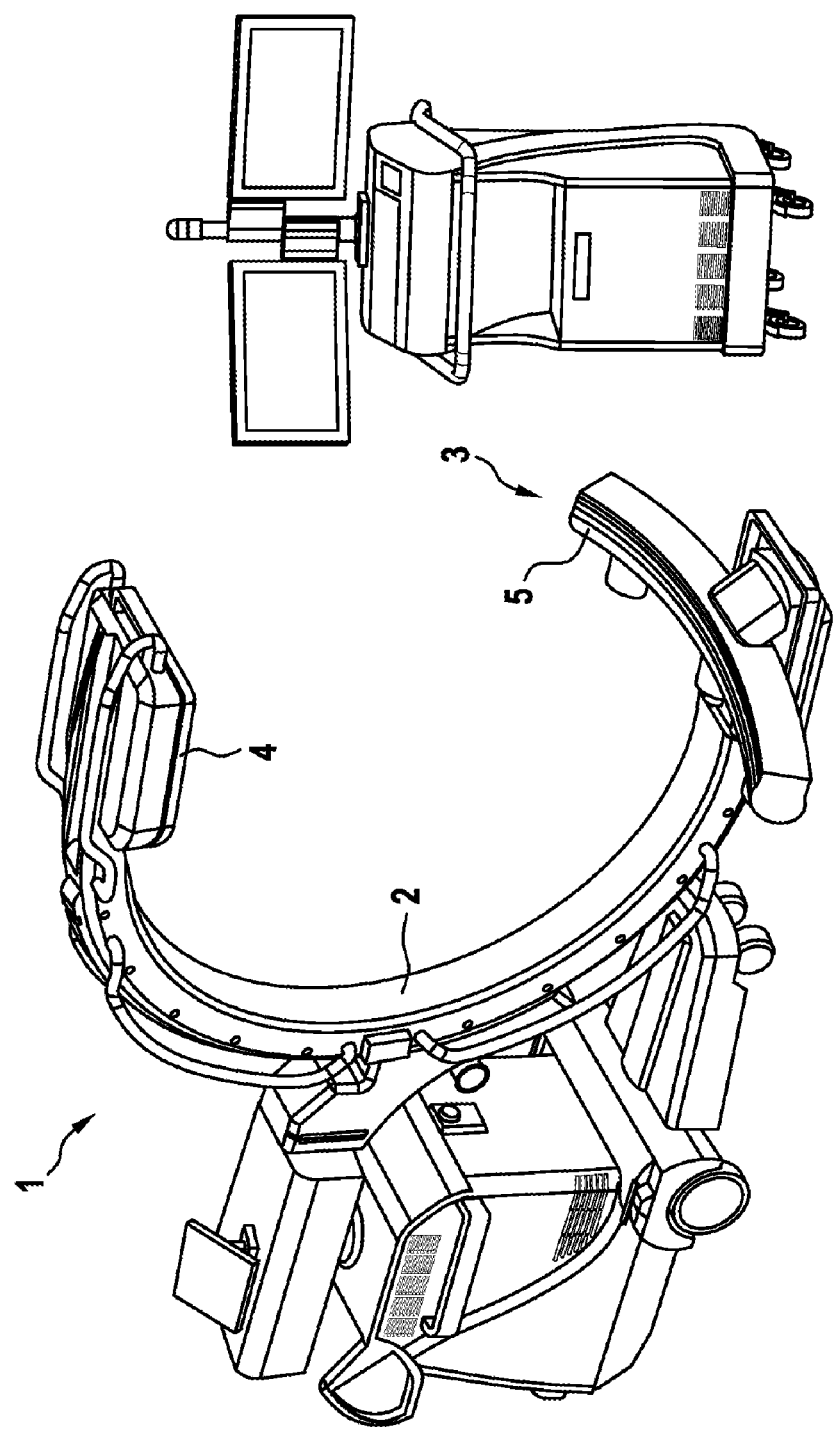
Figure 21:
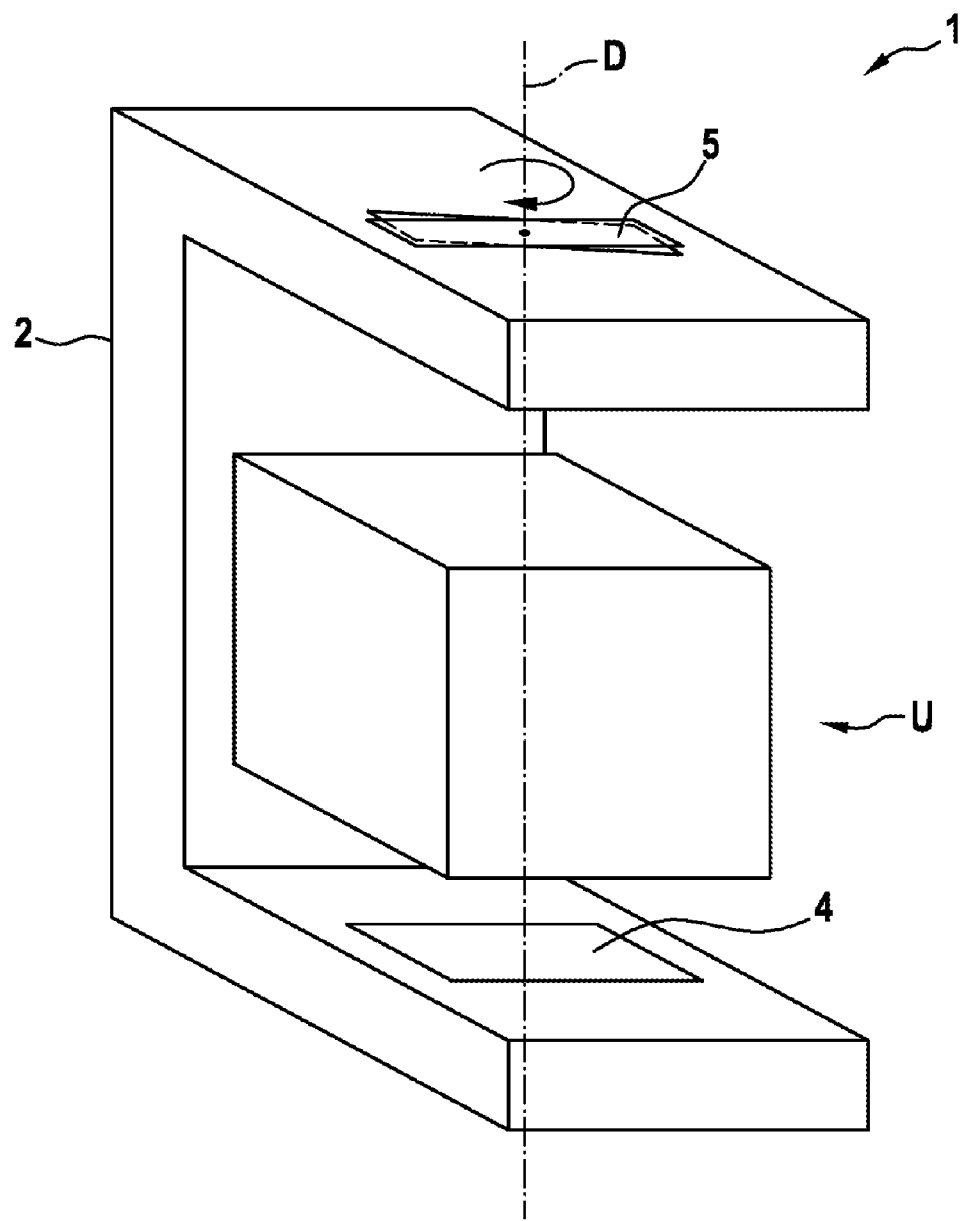
Figure 22:
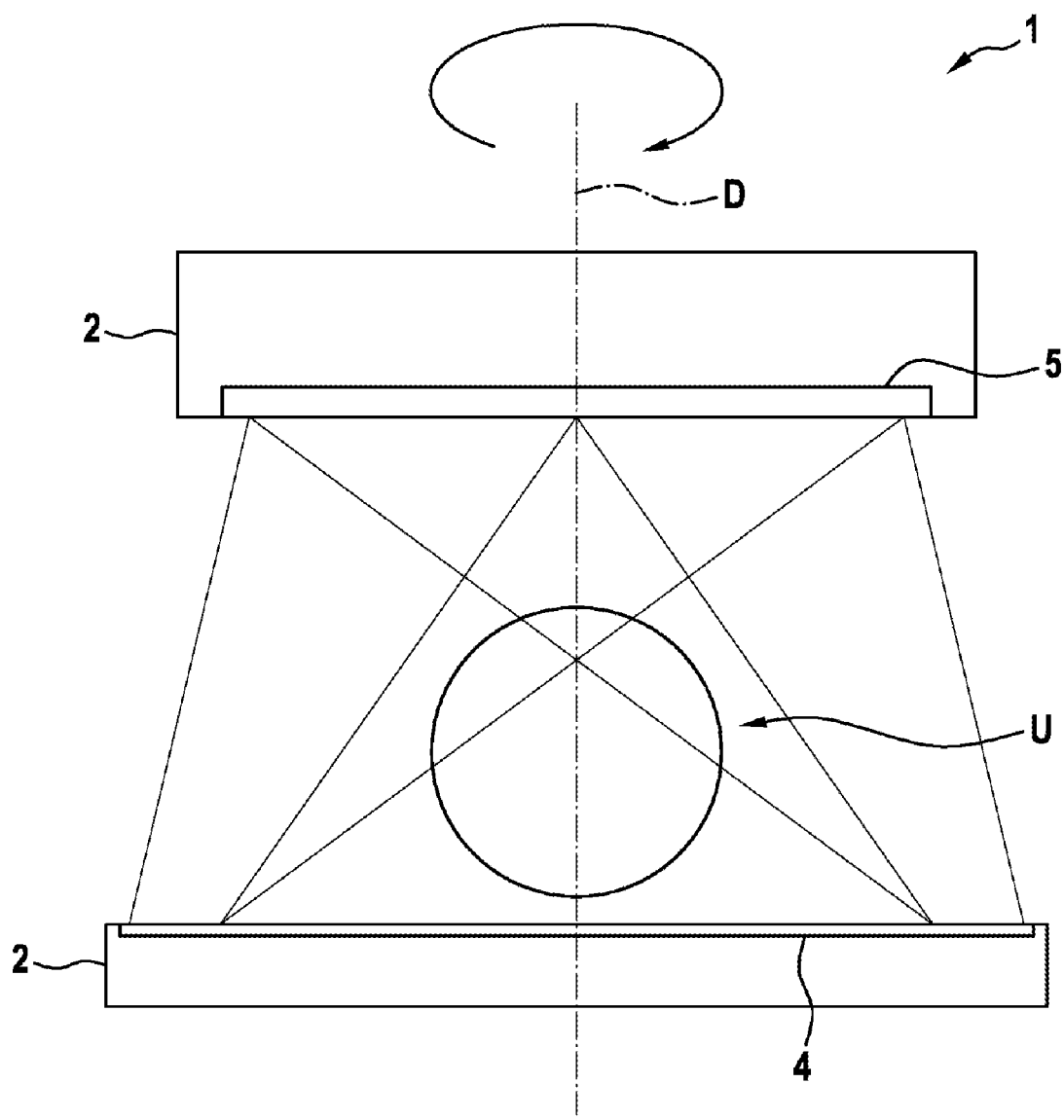
Figure 23:
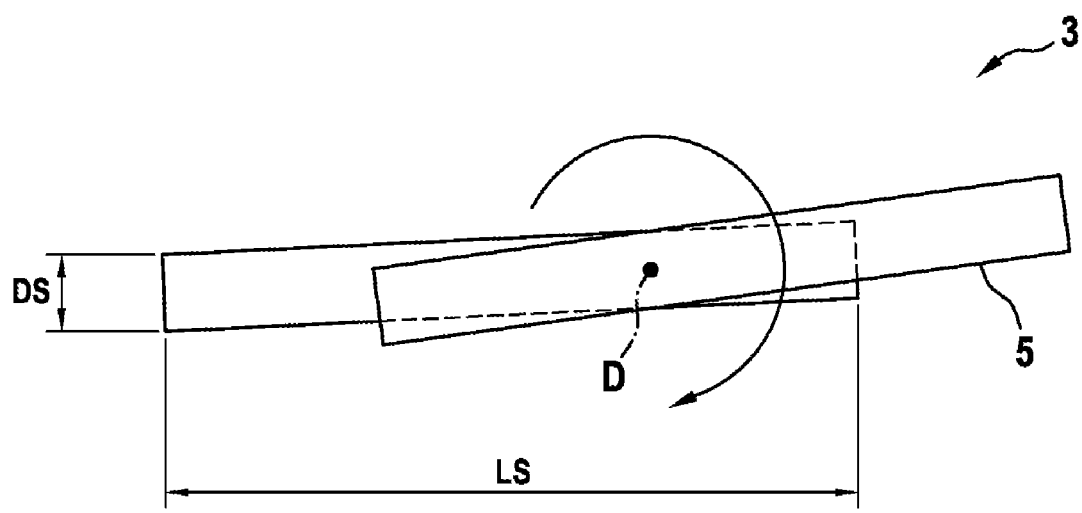
Figure 24:
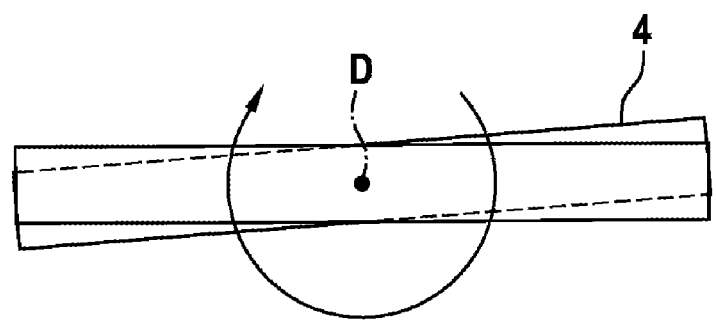
Figure 25:
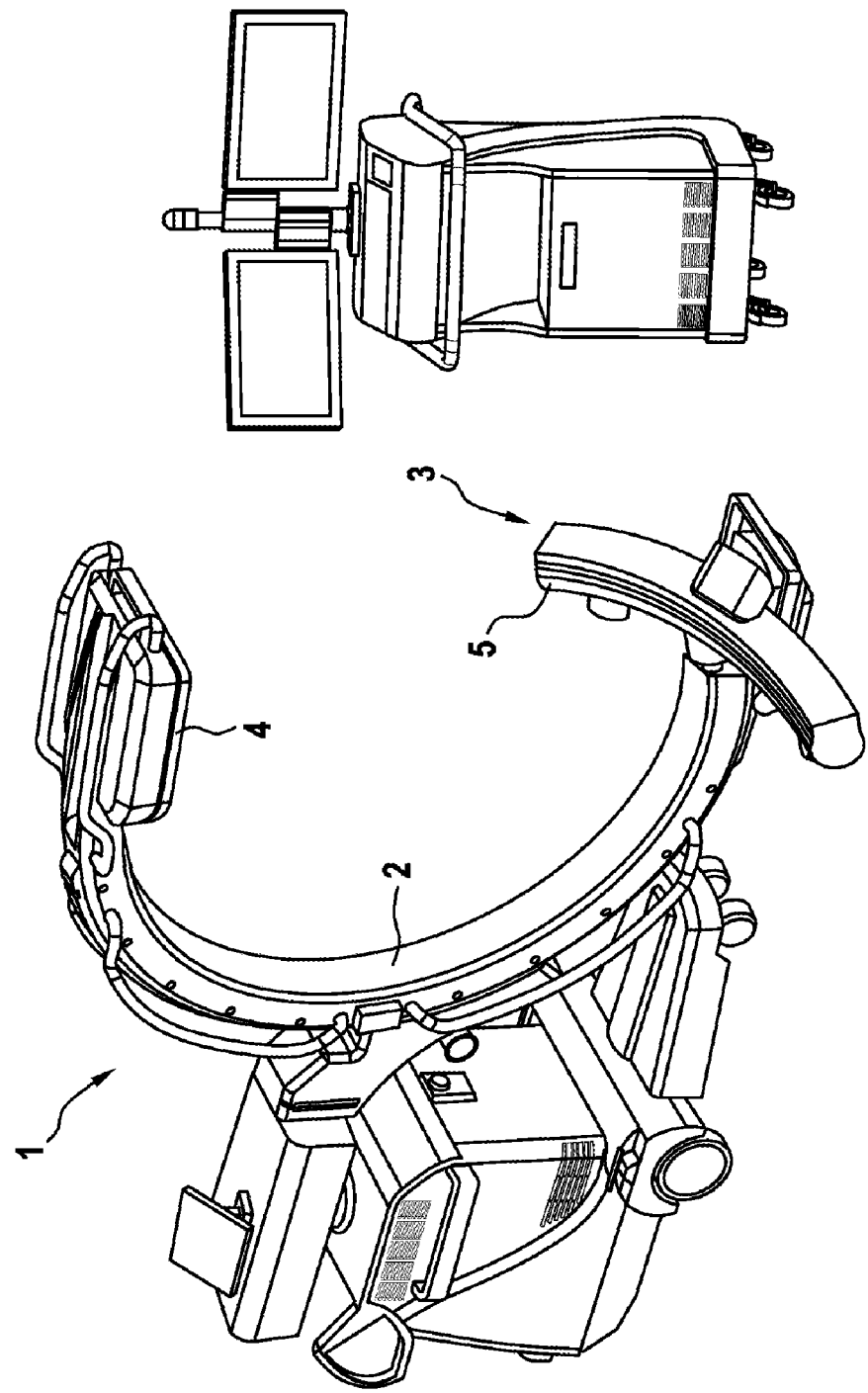

FIG. 21 shows a schematic perspective view of another embodiment of a C-arm X-ray apparatus, FIG. 22 shows a schematic front view of the C-arm X-ray apparatus according to FIG. 22, FIGS. 23 and 24 show components which can be rotated about a joint virtual axis, namely an X-ray emitter and an X-ray detector, respectively, of the C-arm X-ray apparatus according to FIG. 21, FIG. 25 shows the C-arm X-ray apparatus according to FIG. 5 with, compared to FIG. 5, another angular setting of the X-ray emitter about a virtual axis of rotation extending between the X-ray emitter and the X-ray detector.

The following explanations refer to all exemplary embodiment, unless indicated otherwise.

A C-arm X-ray apparatus 1 has a C-arm 2 which can be adjusted in manifold ways and to which an X-ray emitter arrangement 3 and an associated X-ray detector 4 are fastened. Adjustability of the C-arm 2 does not apply to the exemplary embodiment shown in FIGS. 21 to 24. In all exemplary embodiments shown, the C-arm 2 defines a reference plane which is aligned vertically in the arrangement according to FIG. 1 and horizontally in the arrangement according to FIG. 2, for example.

The X-ray emitter arrangement 3 in all exemplary embodiments includes an X-ray emitter 5 of a first type, which includes field emission cathodes with carbon nanotubes (CNT). The X-ray emitter 5 has an elongate shape, optionally bent into an annular shape which is closed or approximately closed. The closed shape can also be formed by multiple X-ray emitters 5. In no case is the ring shape or other annular or frame-like shape formed by at least one X-ray emitter 5 filled in an areal manner, for example in the shape of a square.

A tangent can be placed on a section of the X-ray emitter 5, which section has at least a longitudinal and a tangential direction and is either straight or curved, which tangent is normal relative to the reference plane defined by the C-arm 2. If the X-ray emitter 5 does not have a straight rod-like shape, it defines a plane which is orthogonal to the reference plane.

Figure 1:
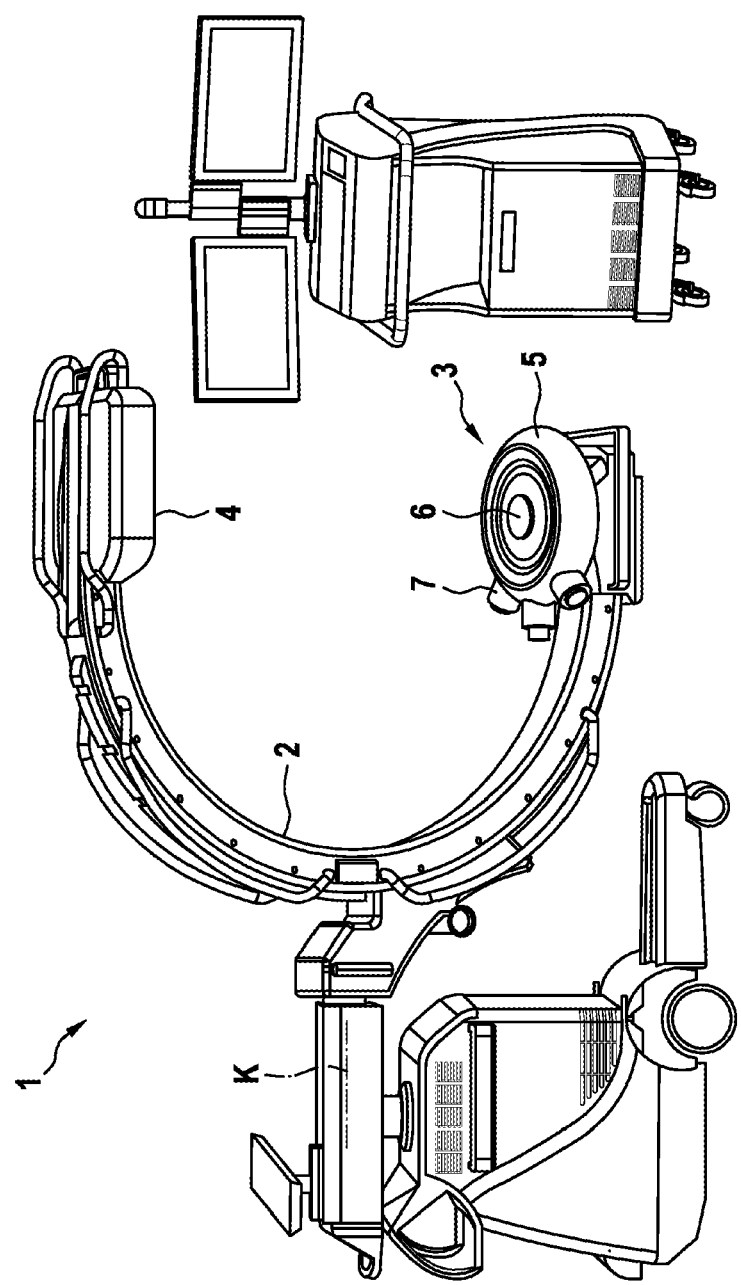
Figure 2:
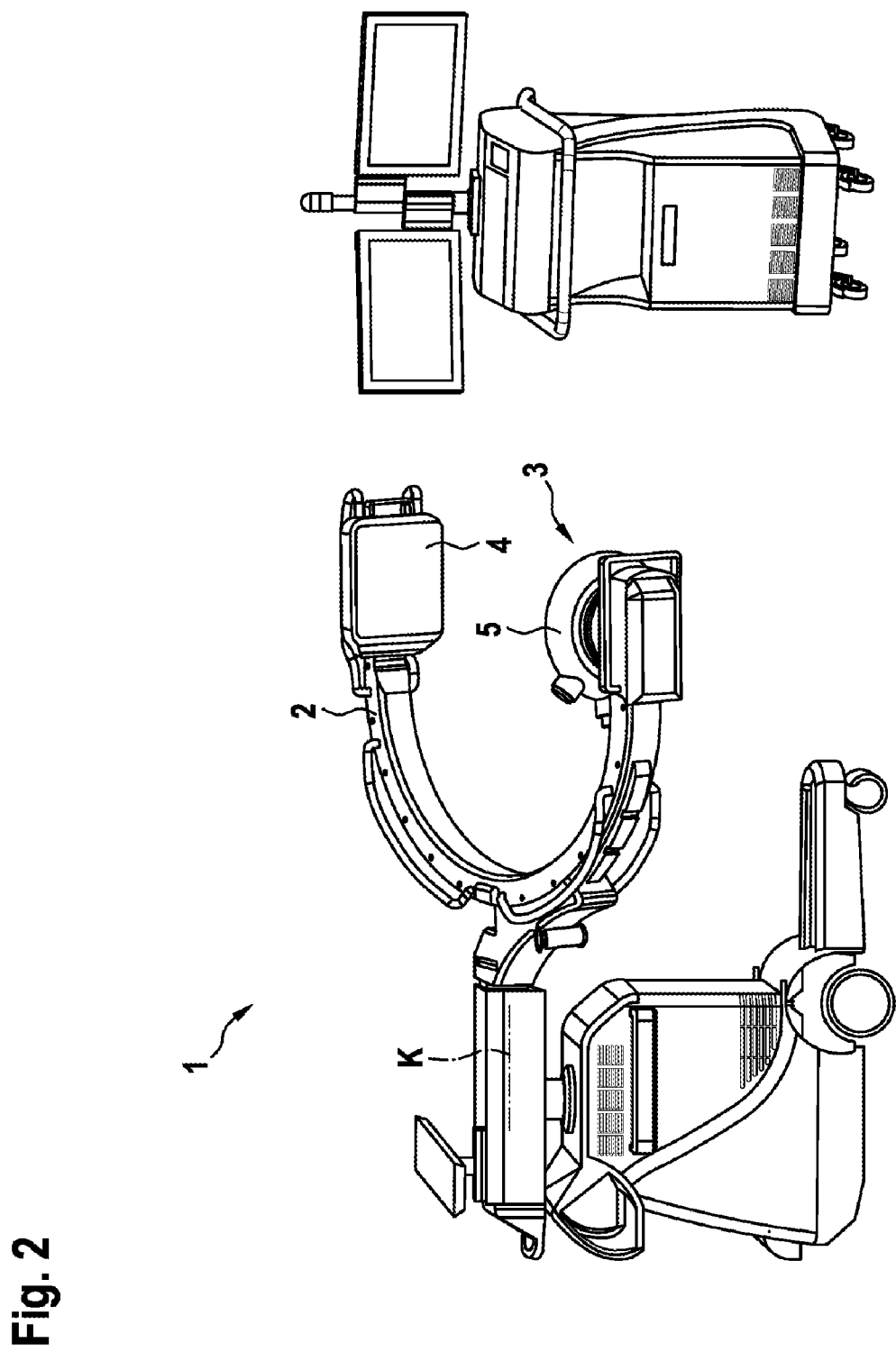
Figure 3:
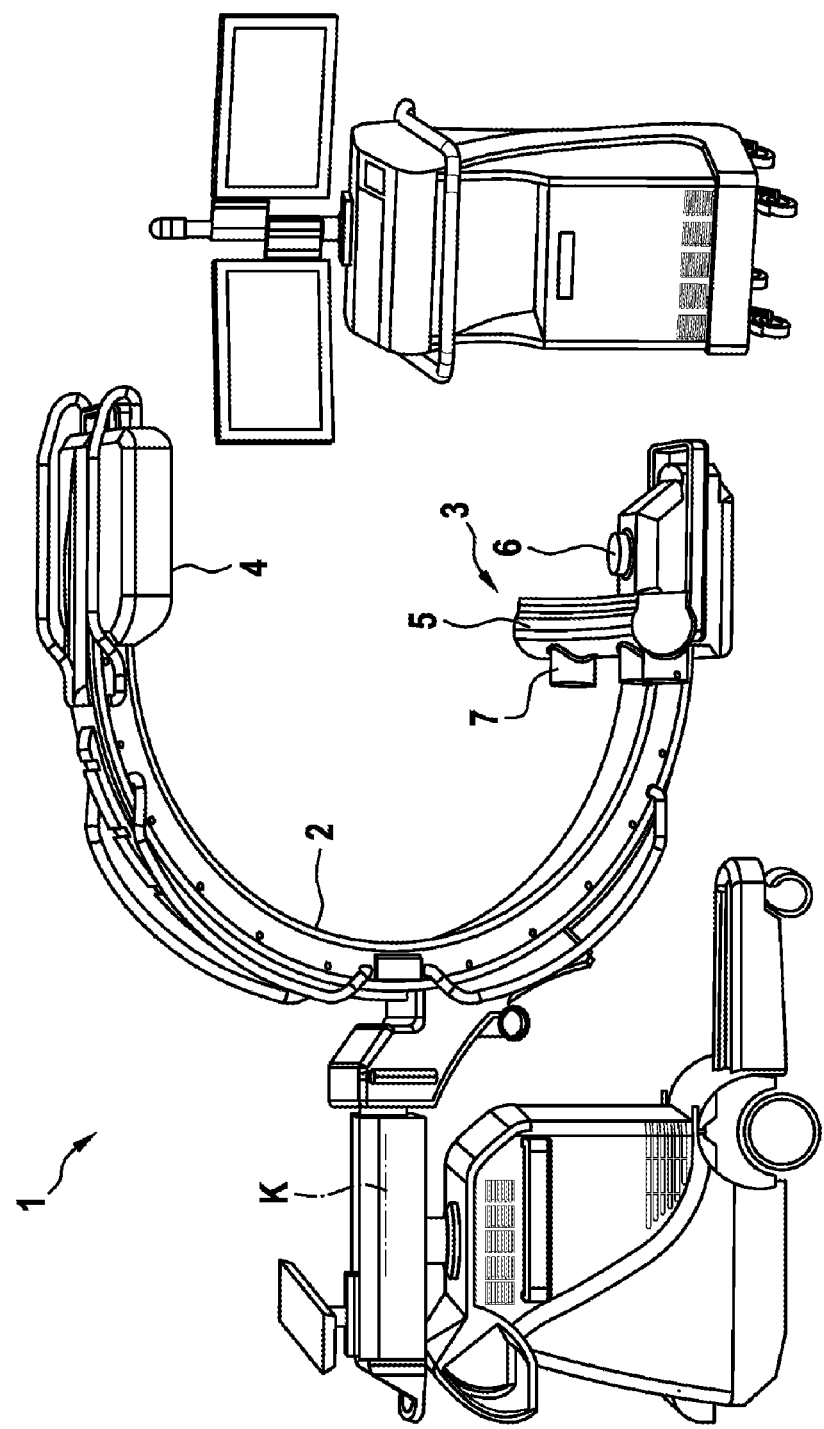
Figure 4:
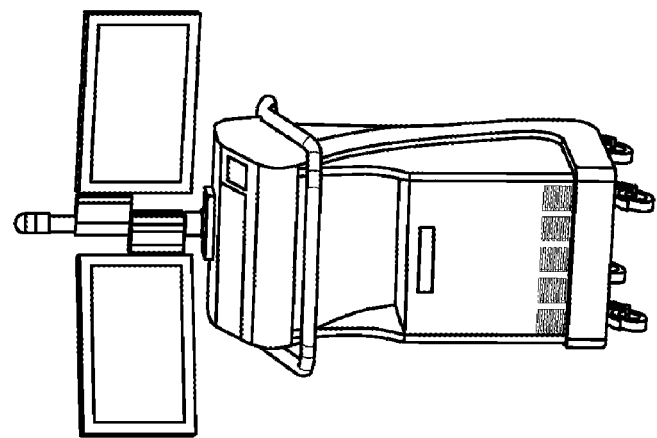
Figure 4:
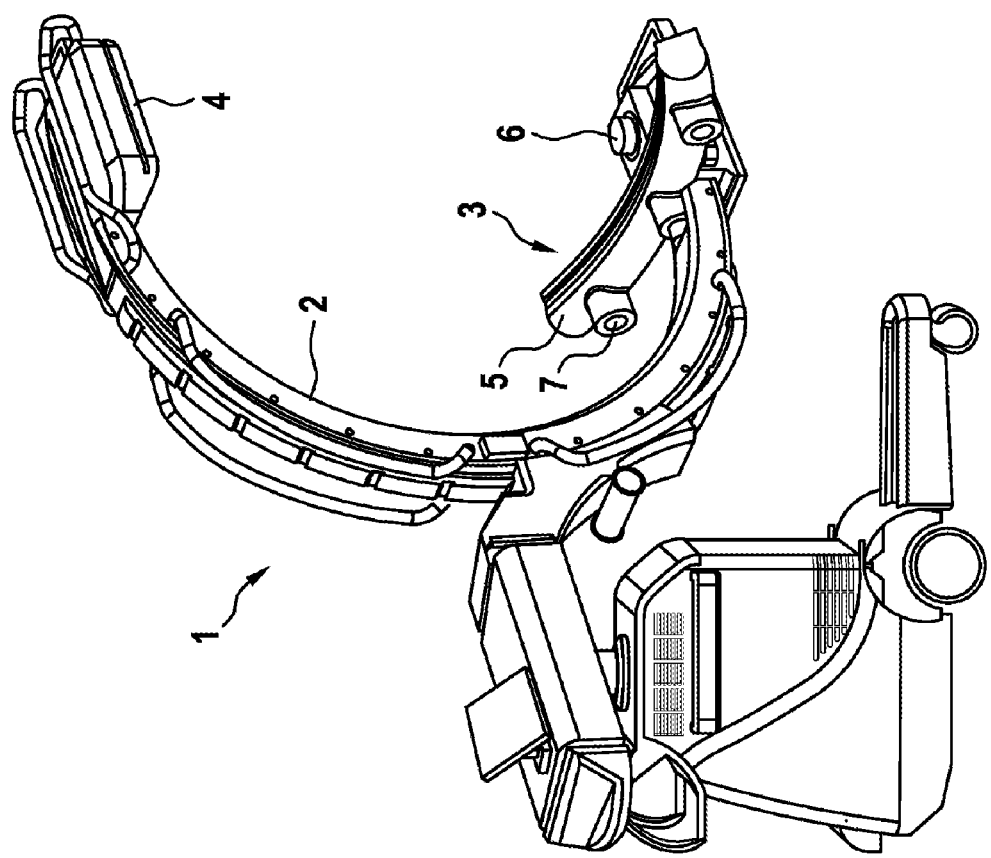
Figure 6:
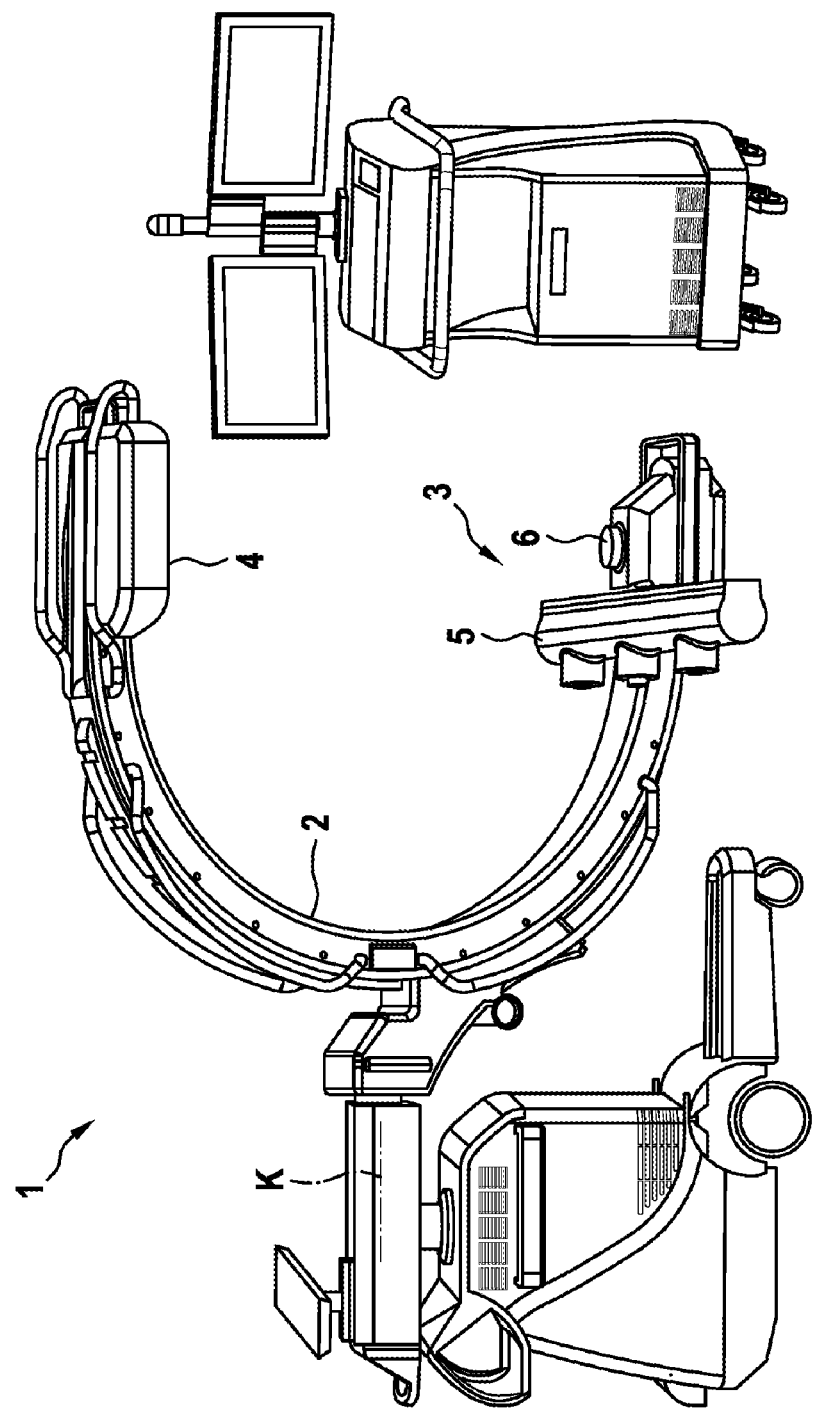

In addition to the X-ray emitter 5 of a first type, the X-ray emitter arrangement 3 includes another X-ray emitter 6 in the embodiments according to FIGS. 1, 3, and 6. This additional X-ray emitter 6 works with an anode that rotates for cooling purposes and is not shown herein, which anode is particularly suited for generating particularly high X-ray doses. The additional X-ray emitter 6, like the annular X-ray emitter 5, comprises nanorods for the emission of electrons. In the exemplary embodiment, three areal electron emitters are arranged in the additional X-ray emitter 6, each comprising nanorods.

In the embodiment according to FIG. 1, the additional X-ray emitter 6 is located centrally in the disc-shaped space surrounded by the first X-ray emitter 5. The central axis of the additional X-ray emitter 6 coincides with the symmetry axis of the annular X-ray emitter 5. The X-ray emitters 5, 6 can be controlled separately.

In the embodiment according to FIG. 3, the X-ray emitter 5 of the first type has an elongate, curved shape. Overall, the X-ray emitter 5 is oriented transversely to the reference plane defined by the C-arm 2. The arc-shaped X-ray emitter 5 defines a plane which is normal to the tilt axis K of the C-arm 2. The tilt axis K lies in the reference plane. The additional X-ray emitter 6 is fastened next to the X-ray emitter 5 of the first type to the C-arm 2 in the case of FIG. 3.

The embodiment according to FIG. 5 differs from the embodiment according to FIG. 3 in that the additional X-ray emitter 6 is eliminated. Likewise, such an additional X-ray emitter 6 could be eliminated in the embodiment according to FIG. 1.

The embodiment according to FIG. 6 resembles the embodiment according to FIG. 3, but in this case the X-ray emitter 5 has a straight, rod-like shape. The longitudinal axis of the rod-shaped X-ray emitter 5 is identical with a surface normal of the reference plane formed by the C-arm 2. An additional, optional X-ray emitter 6 is fastened next to the first X-ray emitter 5 to an end of the C-arm 2 in the arrangement of FIG. 6, like in the arrangement of FIG. 3.

Figure 7:
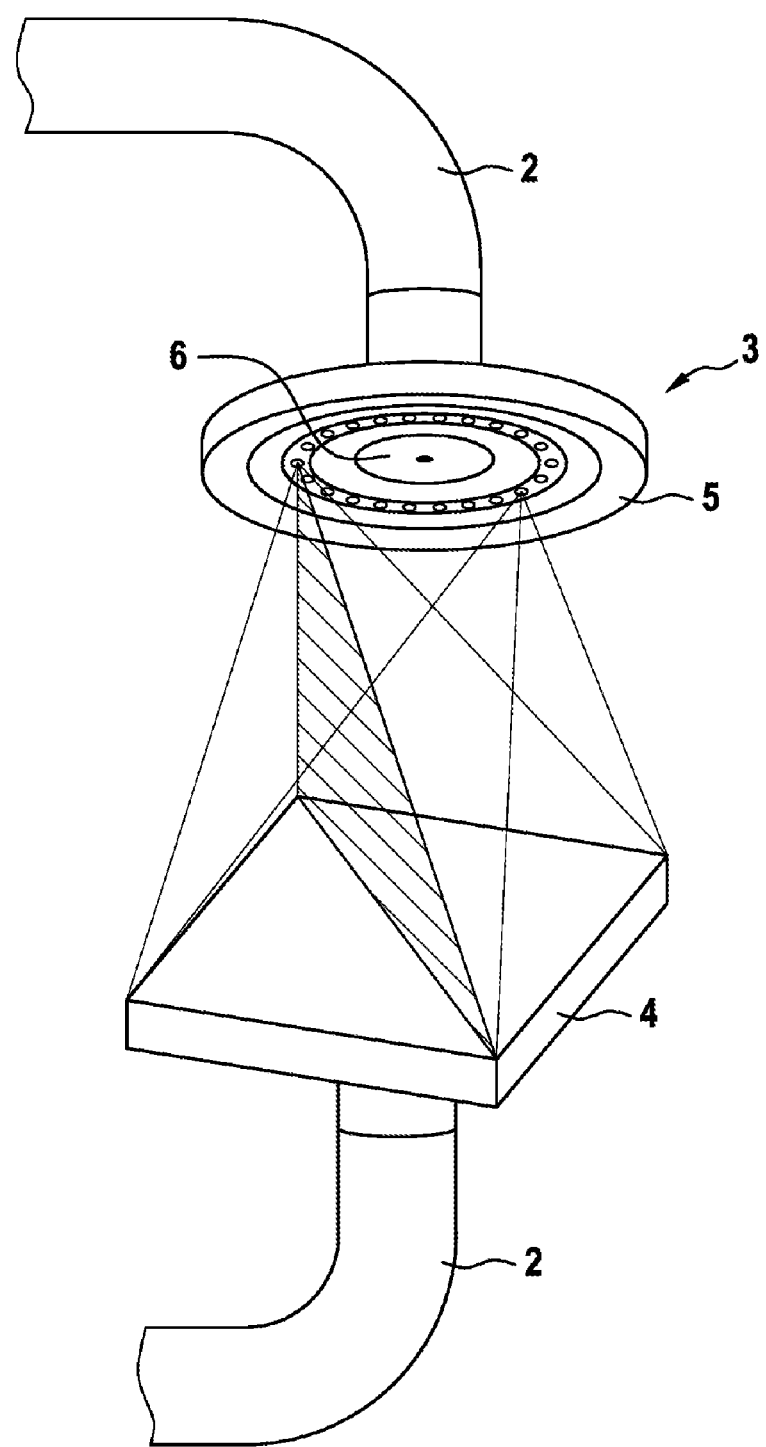

FIG. 7 illustrates the optical path of X-ray radiation emitted by the X-ray emitter 5. Two point sources of X-ray radiation are assumed here. The X-ray radiation propagates from each approximately point-shaped source in such a manner that it impinges on the entire areal detector 4.

Collimator devices, which limit the optical path of the X-ray radiation, are not shown in FIG. 7. Tomography images of an object under examination can be generated from a multitude of individual projection images obtained using a single X-ray source, without changing the local relation between the C-arm 2 and the object under examination. The X-ray emitter 5 according to FIG. 7 forms a total of 96 X-ray sources of exactly defined positions.

Figure 8:
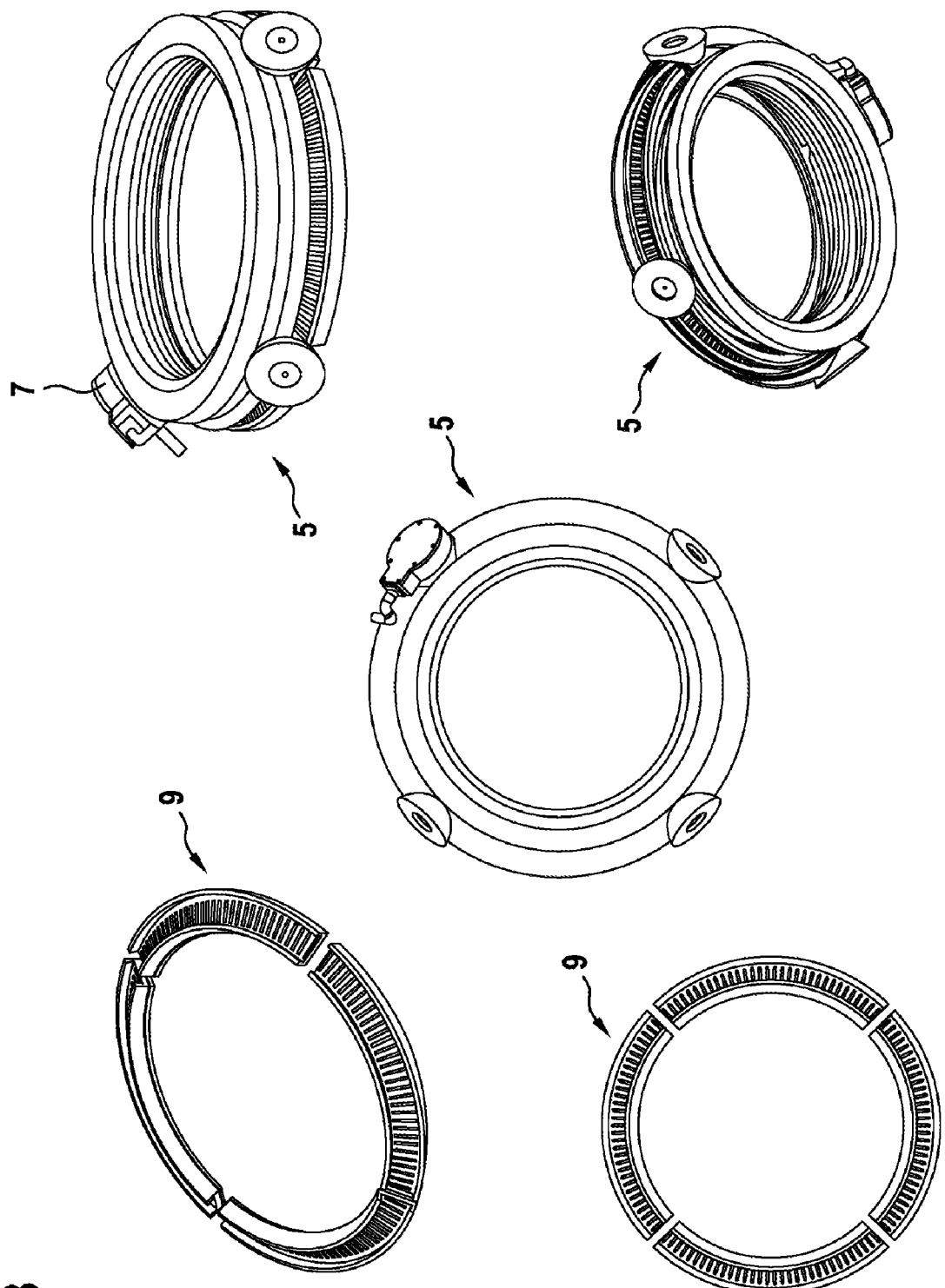
FIG. 8 shows various views, at least of parts, of an annular X-ray emitter.

The X-ray emitter arrangement 3 shown in FIG. 8, suitable for the C-arm X-ray apparatus 1 according to FIG. 1, can be combined, if required, with an additional X-ray emitter 6 not shown here. Vacuum passages are labeled 7, emitter arrangements of the X-ray emitter 5 are labeled 9.

Figure 9:
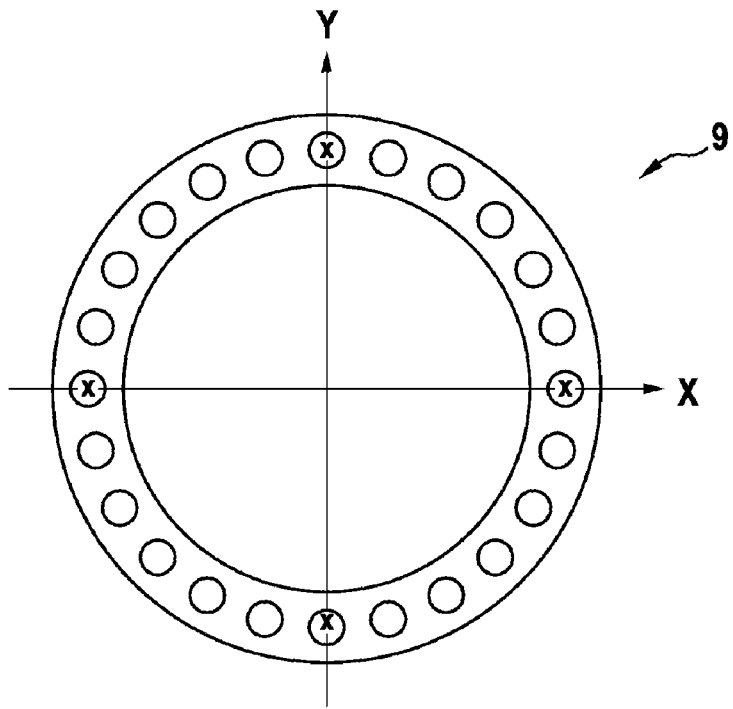
FIGS. 9 to 11 show various modes of operating an annual X-ray emitter.
Figure 10:
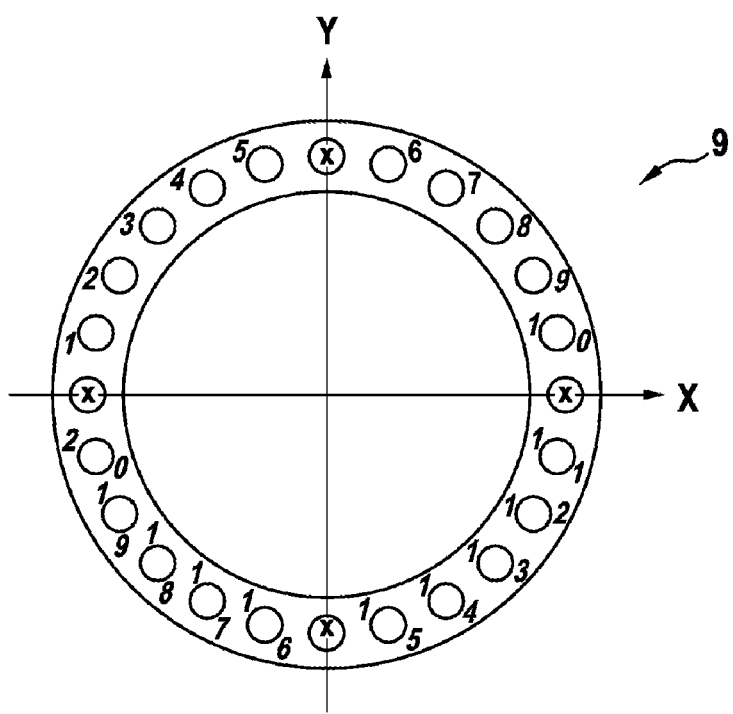
Figure 11:
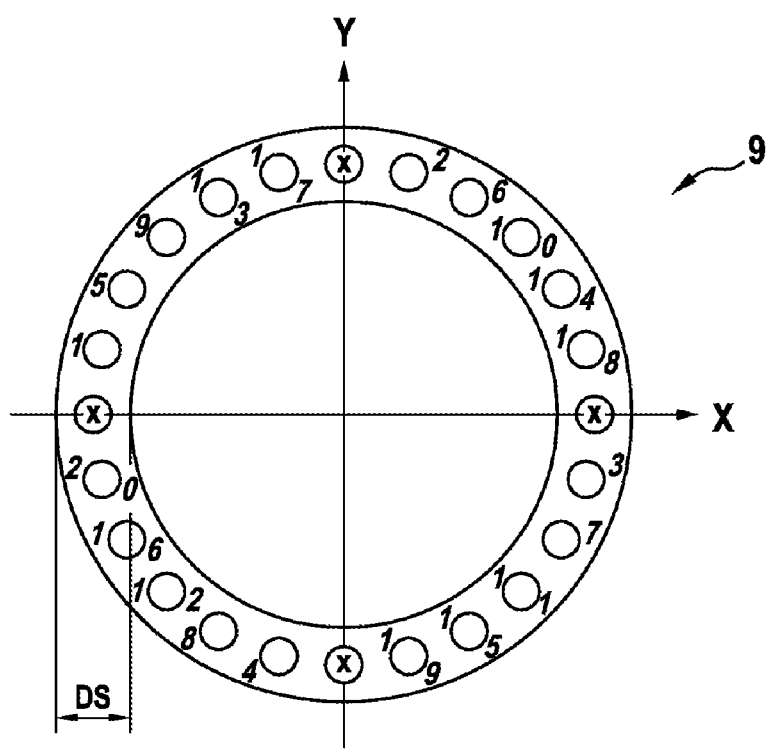

FIGS. 9 to 11 illustrate a potential operating mode of the annular X-ray emitter arrangement 3. All electron emitters of the X-ray emitter arrangement 3 are formed by field emission cathodes with carbon nanotubes (CNT). In a first step, four emitters are activated, for example, as marked in FIG. 9, which emitters are spaced apart from each other at a 90° angle, that is, are located either on the x-axis or on the y-axis. Other projection images may be generated in the next steps, for example according to FIG. 10 or FIG. 11. In the case of FIG. 10, other emitters are activated in circular sequence, starting at the emitter located on the x-axis between the second and third quadrants.

In the case of FIG. 11, on the other hand, emitters located in different quadrants are activated successively, such that always two emitters are activated successively which are at a large distance from each other in the circumferential direction of the X-ray emitter 5, compared to the operating mode of FIG. 10. The operating mode illustrated in FIG. 11 has the advantage that three-dimensional images of acceptable quality can be obtained based on projection images which were generated with only a part of the existing emitters.

Figure 12:
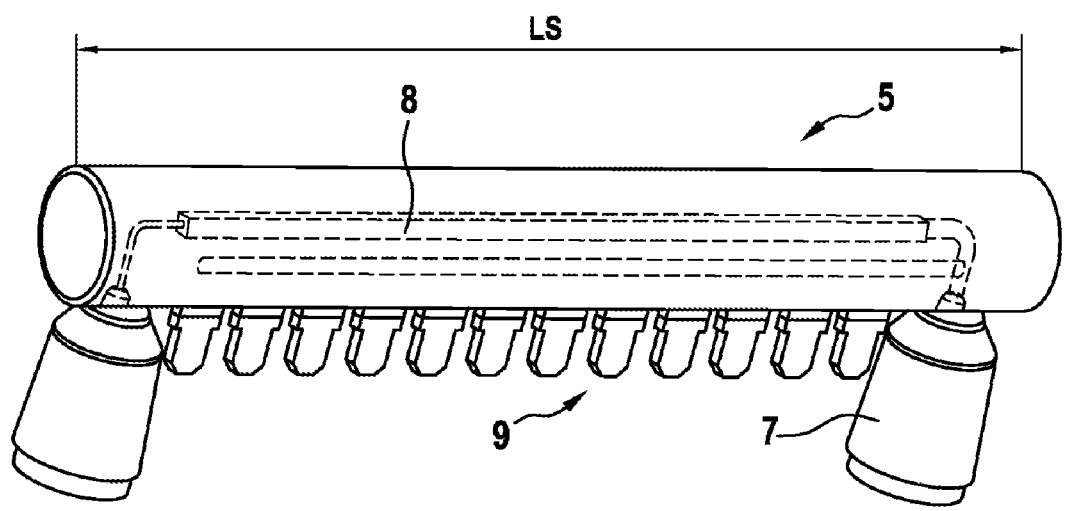
FIG. 12 shows an X-ray emitter having a basic cylindrical shape.
Figure 13:
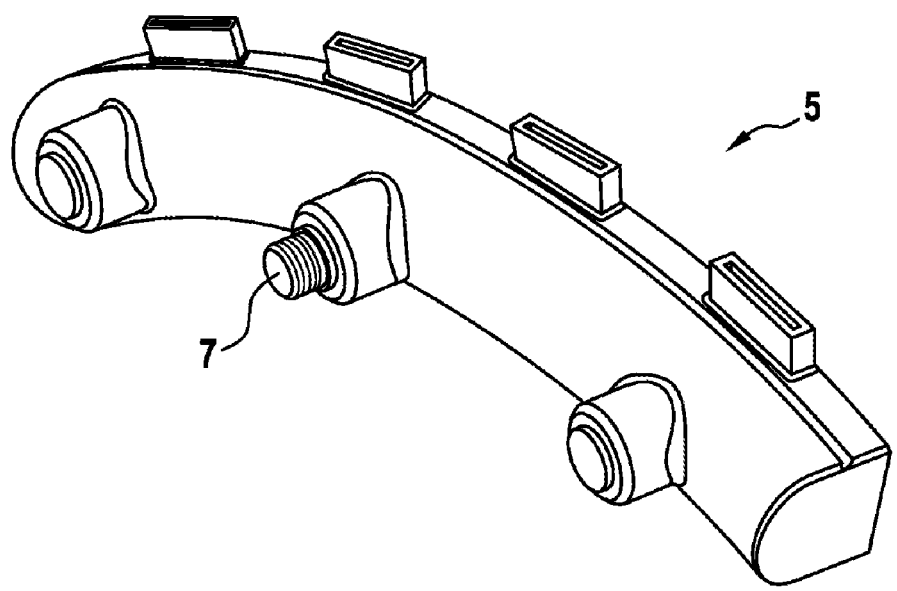
FIG. 13 shows an arched X-ray emitter.

FIGS. 12 and 13 show a partially transparent (FIG. 12) perspective view of the X-ray emitters 5 of FIG. 6 or FIG. 3, respectively. The anode labeled 8 in FIG. 12 of the X-ray emitter 5 is cooled by an electrically conductive oil which flows through the anode 8. Each of the X-ray emitters 5 defines a longitudinal direction, which in the case of FIG. 13 is defined by the tangential direction of the arc defined by the X-ray emitter 5, wherein the tangent is to be placed centrally between both ends of the arc. In the embodiment of FIG. 12, LS represents the overall length of the X-ray emitter 5. The overall length LS is always to be measured in the longitudinal direction of an elongate structure described by the X-ray emitter 5, in the case of FIG. 12 of a cylinder having a circular cross section.

Figure 14:
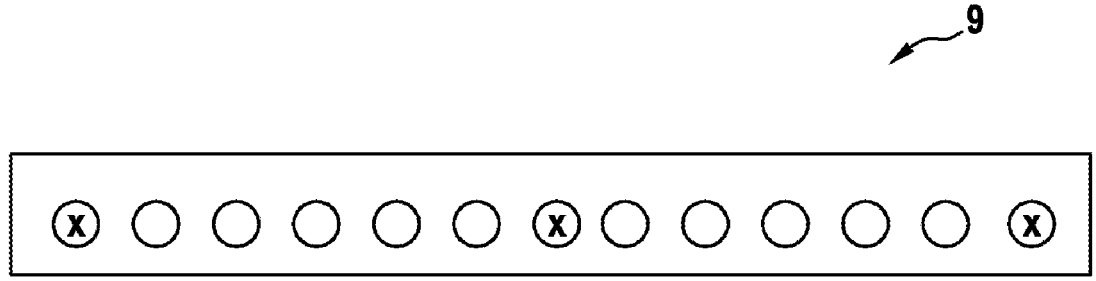
FIG. 14 shows a mode for operating the X-ray emitter according to FIG. 12.

FIG. 14 is to illustrate a potential operating mode of the X-ray emitter 5 of FIG. 12. In this case, initially three CNT cathodes of the X-ray emitter 5 are activated, which are located in the center and on the two ends of the X-ray emitter 5, respectively. There are various options regarding activation of the remaining electron emitters: For example, the remaining electron emitters can be activated in linear sequence, which in principle corresponds to the operating mode in FIG. 10. It is also possible to activate individual emitters one after the other which are at a greater spacing from each other, as has been explained in principle with reference to FIG. 11. Activation of individual electron emitters at random is also possible.

FIGS. 15 to 20 outline other possible shapes of X-ray emitters 5 which can be used for the C-arm X-ray apparatus 1 in addition to the X-ray emitter 5 of FIG. 1. These are a triangular, square, pentagonal, hexagonal, and decagonal shape. Other closed shapes, e.g. an octagon, are possible.

Figure 15:
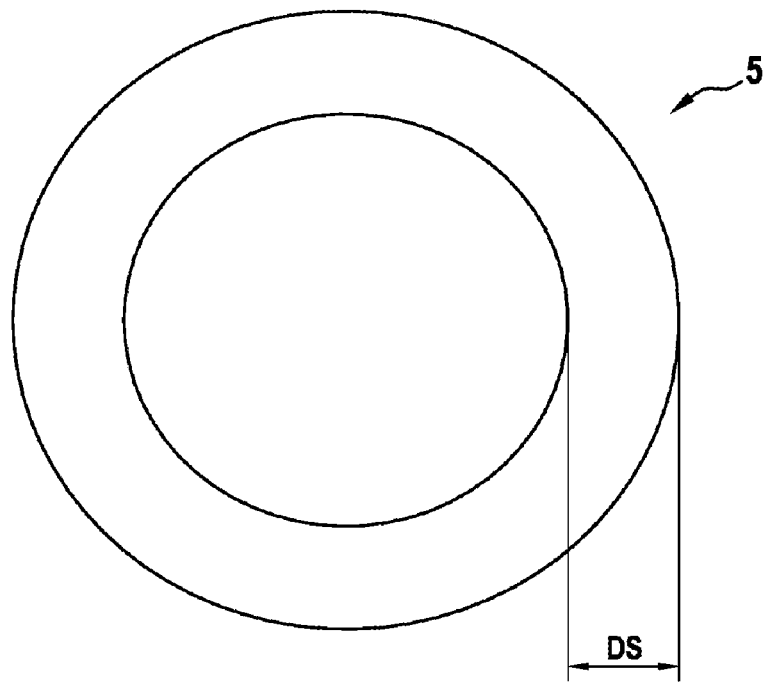
FIGS. 15 to 20 show various basic shapes of other X-ray emitters.
Figure 16:
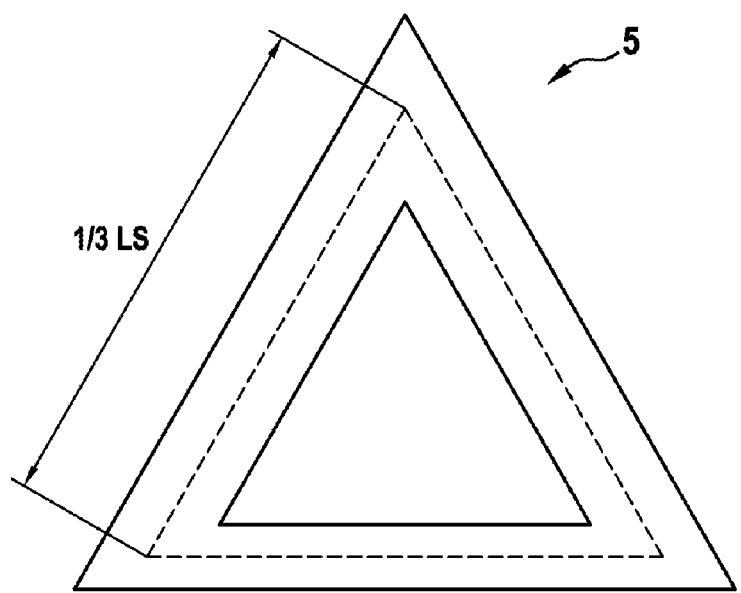
Figure 17:
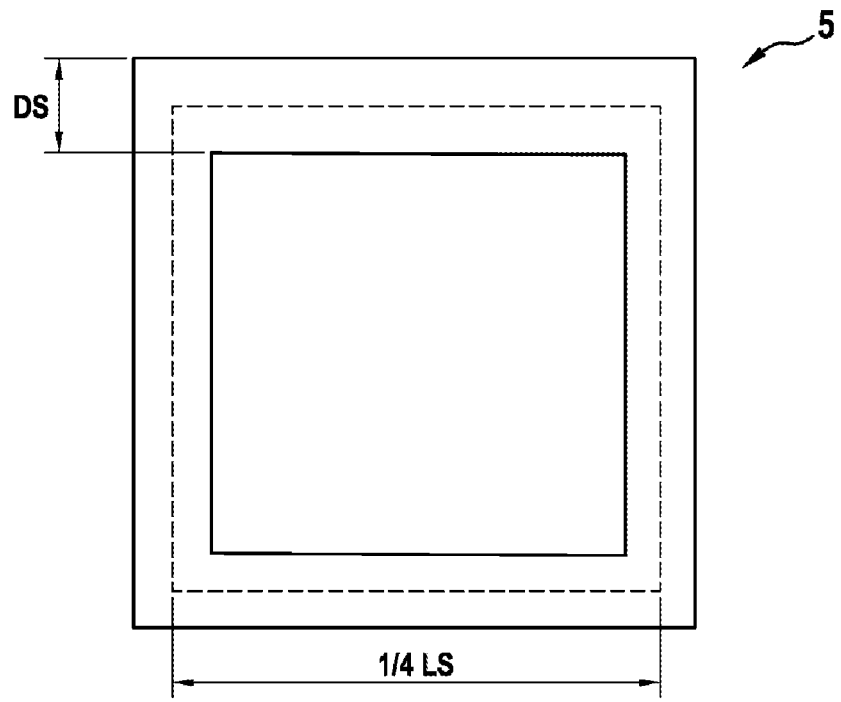
Figure 18:
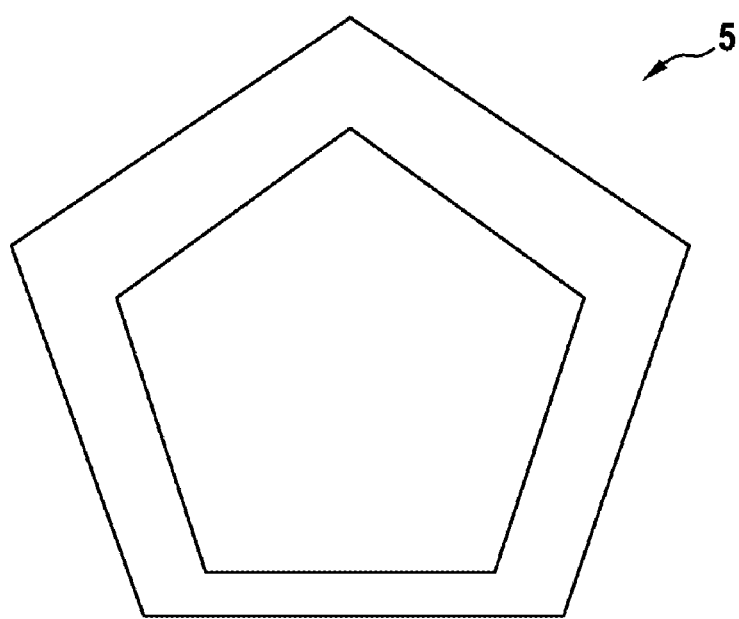
Figure 19:
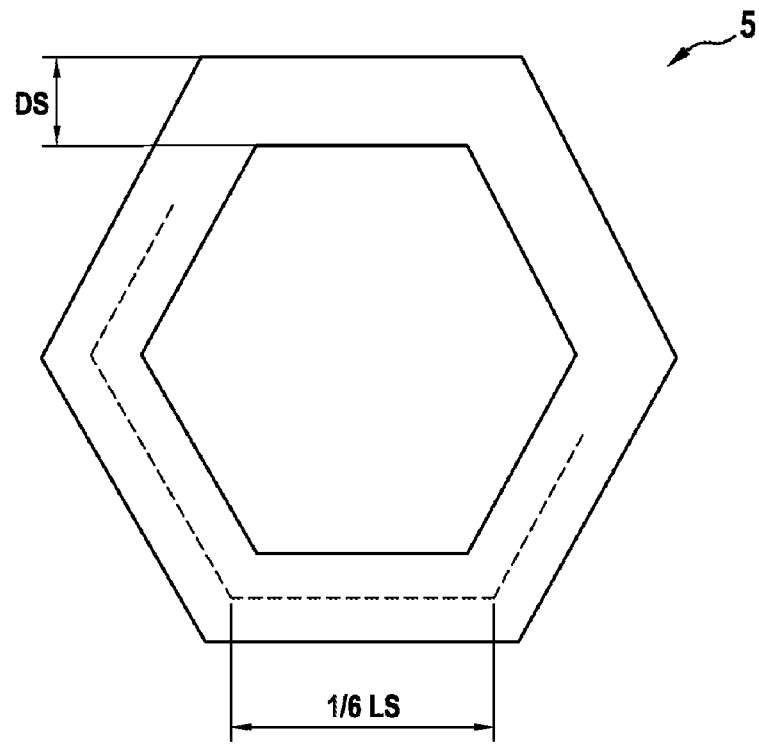
Figure 20:
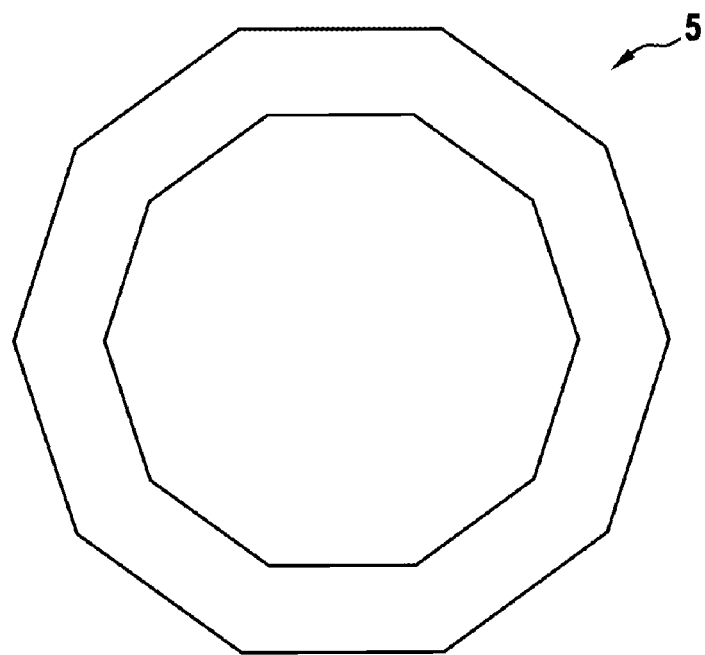

DS designates the diameter of the cross section of the elongate structure of the X-ray emitter 6. In the case of FIG. 15, the elongate structure is a torus. If the elongate structure does not have a circular cross section, as shown in FIGS. 16 to 20, DS is defined as the maximum diameter of the cross section of the elongate structure. The dashed line sometimes shown along which the overall extension of LS is to be measured is bent in the case of a polygonal X-ray emitter 5 in accordance with the respective polygonal shape. In all other cases, the extension LS is more than the quadruple of the diameter DS.

In the cases outlined in FIGS. 15 to 20, the optional, additional X-ray emitter 6 is preferably located in the center of the respective shape, like in the arrangement of FIG. 1. Thus the reference plane defined by the C-arm 2 intersects with the additional X-ray emitter 6, whereas the X-ray emitter 5 which works with CNT emitters protrudes on both sides from this reference plane.

In the exemplary embodiment shown in FIGS. 21 to 24, the C-arm 2 is fixedly arranged in space during an X-ray examination. Only the X-ray emitter 5 and the X-ray detector 4 can be pivoted about a joint virtual axis of rotation D. Synchronization of the pivoting movements of the X-ray emitter 5 and the X-ray detector 4 is performed electronically. As is apparent from FIG. 21, the X-ray emitter 5 and the X-ray detector 4 each have an elongate basic shape. In the arrangement according to FIG. 21, the X-ray emitter 5 and the X-ray detector 4 are oriented transversely to the reference plane defined by the C-arm 2. In the view of FIG. 22, the reference plane is orthogonal to the drawing plane, wherein the axis of rotation D lies in the reference plane. The axis of rotation D intersects an area under examination U located between the X-ray emitter 5 and the X-ray detector 4.

The X-ray emitter 5 of the X-ray apparatus 1 of FIG. 21 is suitable for emitting fan-shaped X-ray beams, wherein the plane in which the fan is located can be adjusted in manifold ways during a X-ray recording by discontinuous and continuous pivoting of the X-ray emitter 5 about the axis of rotation D. The small masses and moments of inertia of the X-ray emitter 5 and the X-ray detector 4 compared to the entire C-arm 2 facilitate the recording of successive X-ray images in short cycles, at different angular settings of the X-ray emitter 5 and the X-ray detector 4, wherein the assembly formed by the X-ray emitter 5 and the X-ray detector 4 can be stationary for each X-ray image. A set of projections generated in this manner facilitates the provision of sectional images and volume data with little equipment compared to conventional systems. A line detector is provided as X-ray detector 4 in the exemplary embodiment shown in FIG. 21.

The X-ray emitter 5, like the X-ray detector 4, can be adjusted in an angular range of at least +20° to −20°, as regards adjustment about the axis of rotation D. Adjustment can be performed in 40 steps, for example. A multitude of potential settings results, if in addition, which is not apparent in FIG. 21, a means for adjustment in the tangential direction of the C-arm 2 is provided, that is, about an imaginary transverse axis which is normal relative to the reference plane, that is, in the longitudinal direction of the X-ray emitter 5 and the X-ray detector 4. If the C-arm can for example be adjusted about the transverse axis in 60 steps, there are 40×60=2,400 potential settings of the assembly formed of the X-ray emitter 5 and the X-ray detector 4.

Adjustment of the X-ray emitter 5 about the axis of rotation D, which intersects the X-ray emitter 5 and the X-ray detector 4 in the center, is also illustrated in FIG. 25, which shows the exemplary embodiment according to FIG. 5. Emitter adjustability about the axis of rotation 5 can be provided in all other embodiments of the C-arm X-ray apparatus 1 having an elongate, straight or curved X-ray emitter 5.

LIST OF REFERENCE NUMERALS

1 C-arm X-ray apparatus
2 C-arm
3 X-ray emitter arrangement
4 X-ray detector
5 X-ray emitter of the first type (with nanorods)
6 additional X-ray emitter
7 vacuum passage
8 anode
9 emitter arrangement
DS diameter of the cross section of the elongate structure of the X-ray emitter
K tilt axis
LS extension in the longitudinal direction of the elongate structure of the X-ray emitter
U area under examination

The invention claimed is:

1. A C-arm X-ray apparatus comprising an X-ray emitter and an X-ray detector, which are held on a C-shaped arm extending in a reference plane, wherein the X-ray emitter includes nanorods as electron emitters and defines an elongate structure which is at least partially oriented along a surface normal to the reference plane;
wherein the X-ray emitter rotates relative to the reference plane, and the X-ray detector rotates relative to the reference plane, wherein the X-ray emitter and the X-ray detector are coaxially aligned and rotate about a joint axis of rotation passing through the X-ray emitter and the X-ray detector, and wherein the X-ray emitter, the X-ray detector, and the joint axis of rotation are positioned in the reference plane of the C-shaped arm.

2. The X-ray apparatus according to claim 1, wherein the X-ray emitter has a straight elongate shape.

3. The X-ray apparatus according to claim 1, wherein the X-ray emitter is annular, wherein two tangents placed onto the X-ray emitter each represent a surface normal to the reference plane.

4. The X-ray apparatus according to claim 1, wherein the X-ray emitter has a polygonal shape.

5. The X-ray apparatus according to claim 1, wherein an entire extension of the X-ray emitter, as measured in each section of the elongate structure in a longitudinal direction, is at least four times a diameter of the cross section of the X-ray emitter as measured across the elongate structure.

6. The X-ray apparatus according to claim 1, wherein carbon nanotubes (CNT) are provided as nanorods for the emission of electrons.

7. The X-ray apparatus according to claim 6, wherein at least a part of the nanorods is configured as single or multi-wall carbon nanotubes or single or multi-wall heteronitrogen carbon nanotubes.

8. The X-ray apparatus according to claim 6, wherein at least a part of the nanorods contains borides of rare earth metals, metal oxides, metal sulfides, nitrides, carbides, or silicon.

9. The X-ray apparatus according to claim 6, wherein the nanorods have a length of less than 20 μm and a diameter of less than 10 nm, wherein a density relative to an area of a cathode configured for emission of electrodes of at least $10^6$ nanorods per $cm^2$.

10. The X-ray apparatus according to claim 1, wherein the X-ray emitter is annular or polygonal and has a cathode which contains nanorods, and wherein an additional X-ray emitter has a cathode which contains nanorods.

11. The X-ray apparatus according to claim 1, wherein the X-ray emitter and the X-ray detector are electronically synchronized with respect to rotations about the axis of rotation.

12. The X-ray apparatus according to claim 1, wherein the C-shaped arm is adjusted in a tangential direction, about an imaginary pivot axis oriented transversely to the reference plane.

13. A method for operating the X-ray apparatus according to claim 12, wherein multiple X-ray images are created which differ from each other, both with respect to a setting of the C-shaped arm in the tangential direction and with respect to an angular setting of the X-ray emitter and the X-ray detector relative to the axis of rotation located in the reference plane.

14. The method according to claim 13, wherein when creating a set of X-ray images, the C-shaped arm is fixed in a first quantity of various positions with respect to adjustment in the tangential direction, and wherein X-ray images with a second quantity of various angular settings of X-ray emitter and X-ray detector are generated in each of the positions.

15. The X-ray apparatus according to claim 1, wherein the joint axis of rotation of the X-ray emitter and the X-ray detector passes through a center of the X-ray emitter and the X-ray detector.

16. The X-ray apparatus according to claim 1, wherein the C-shaped arm further rotates about a C-shaped arm tilt axis in the reference plane.

17. The X-ray apparatus according to claim 16, wherein the C-shaped arm tilt axis extends horizontally in the reference plane.

18. The X-ray apparatus according to claim 16, wherein the X-ray emitter lies in a plane transverse to the reference plane and normal to the C-shaped arm tilt axis.

19. The X-ray apparatus according to claim 16, wherein the X-ray emitter has an elongate, curved shape and lies in a plane transverse to the reference plane and normal to the C-shaped arm tilt axis.

20. A C-arm X-ray apparatus comprising an X-ray emitter and an X-ray detector, which are held on a C-shaped arm extending in a reference plane, wherein the X-ray emitter includes nanorods as electron emitters and defines an elongate structure which is at least partially oriented along a surface normal to the reference plane;
wherein the X-ray emitter rotates, and the X-ray detector rotates, wherein the X-ray emitter and the X-ray detector are coaxially aligned and rotate about a joint axis of rotation passing through the X-ray emitter and the X-ray detector, and are positioned in the reference plane of the C-shaped arm;
wherein the X-ray emitter has a curved elongate shape which defines a plane orthogonal relative to the reference plane.

21. A C-arm X-ray apparatus comprising an X-ray emitter and an X-ray detector, which are held on a C-shaped arm extending in a reference plane, wherein the X-ray emitter includes nanorods as electron emitters and defines an elongate structure which is at least partially oriented along a surface normal to the reference plane;
wherein the X-ray emitter rotates, and the X-ray detector rotates, wherein the X-ray emitter and the X-ray detector are coaxially aligned and rotate about a joint axis of rotation passing through the X-ray emitter and the X-ray detector, and are positioned in the reference plane of the C-shaped arm;
wherein an additional X-ray emitter is provided in addition to the X-ray emitter containing nanorods, the additional X-ray emitter comprising carbon nanotubes (CNT).

22. The X-ray apparatus according to claim 21, wherein the X-ray emitter is annular or polygonal, and wherein two tangents placed onto the X-ray emitter each represent a surface normal to the reference plane, and the additional X-ray emitter is arranged centrally relative to the annular or polygonal X-ray emitter.

23. The X-ray apparatus according to claim 21, wherein the additional X-ray emitter has a rotating anode.

\* \* \* \* \*